US009392930B2

(12) United States Patent
Lei et al.

(10) Patent No.: US 9,392,930 B2
(45) Date of Patent: Jul. 19, 2016

(54) ENDOSCOPE WITH ADJUSTABLE VIEWING ANGLE

(75) Inventors: Fang Lei, Durchhausen (DE); Ulrich Weiger, Rangendingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 124 days.

(21) Appl. No.: 13/198,483

(22) Filed: Aug. 4, 2011

(65) Prior Publication Data

US 2012/0035422 A1 Feb. 9, 2012

(30) Foreign Application Priority Data

Aug. 4, 2010 (DE) .......................... 10 2010 033 427

(51) Int. Cl.
| | | |
|---|---|---|
| *A61B 1/00* | (2006.01) | |
| *A61B 1/06* | (2006.01) | |
| *A61B 1/07* | (2006.01) | |
| *G02B 23/24* | (2006.01) | |
| *G02B 6/35* | (2006.01) | |

(52) U.S. Cl.
CPC ........... *A61B 1/00126* (2013.01); *A61B 1/0019* (2013.01); *A61B 1/00163* (2013.01); *A61B 1/00181* (2013.01); *A61B 1/0669* (2013.01); *A61B 1/07* (2013.01); *G02B 23/2407* (2013.01); *G02B 6/3524* (2013.01); *G02B 6/3528* (2013.01)

(58) Field of Classification Search
CPC ................ A61B 17/00234; A61B 1/00183; A61B 1/042; A61B 1/04; A61B 1/05
USPC ......... 600/103, 109, 427, 385, 476, 170–176, 600/167–168
See application file for complete search history.

(56) References Cited

U.S. PATENT DOCUMENTS

| 3,880,148 | A | * | 4/1975 | Kanehira et al. ............... 600/173 |
|---|---|---|---|---|
| 4,718,417 | A | * | 1/1988 | Kittrell et al. ..................... 606/7 |
| 5,377,040 | A | * | 12/1994 | Naganuma ............... 359/489.07 |
| 6,055,451 | A | | 4/2000 | Bambot et al. |
| 6,222,970 | B1 | * | 4/2001 | Wach et al. ..................... 385/115 |
| 6,371,909 | B1 | * | 4/2002 | Hoeg et al. ..................... 600/173 |
| 6,560,013 | B1 | * | 5/2003 | Ramsbottom ................ 359/431 |
| 7,808,717 | B2 | * | 10/2010 | Kuiper et al. ................. 359/665 |
| 2002/0107448 | A1 | | 8/2002 | Gandjbakhche et al. |
| 2003/0152312 | A1 | * | 8/2003 | Zhou .................... G02B 6/3524 385/16 |

FOREIGN PATENT DOCUMENTS

DE      60015375 T2    2/2006

OTHER PUBLICATIONS

German Search Report; Application No. DE 10 2010 033 427.8; Issued: Jun. 6, 2011; 3 pages.

* cited by examiner

*Primary Examiner* — John P Leubecker
*Assistant Examiner* — Rajaa El Alami
(74) *Attorney, Agent, or Firm* — Whitmyer IP Group LLC

(57) ABSTRACT

An endoscope with adjustable viewing angle includes one of a number of light outlet devices on the distal end of the endoscope, such that the light outlet devices are configured and positioned to conduct illuminating light emerging from different light outlet devices into at least partly different solid angles, several lightwave conductors to conduct illuminating light to the light outlet devices and a light splitting device for controllably switching illuminating light into one or more of the number of lightwave conductors.

22 Claims, 3 Drawing Sheets

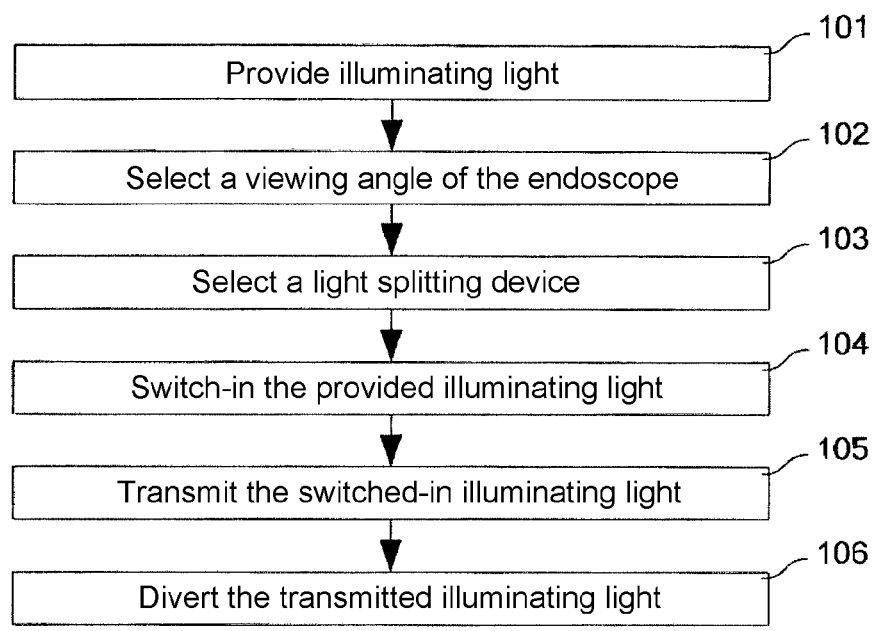

ENDOSCOPE WITH ADJUSTABLE VIEWING ANGLE

CROSS-REFERENCE TO RELATED APPLICATIONS

The present application claims priority of German patent application No. 10 2010 033 427.8 filed on Aug. 4, 2010.

FIELD OF THE INVENTION

The present invention relates to an endoscope with adjustable viewing angle and a method for illuminating an adjustable visual field.

BACKGROUND OF THE INVENTION

Along with endoscopes for medical and non-medical technical applications, whose viewing angle is parallel to the longitudinal axis of the endoscope shaft, endoscopes with other fixed viewing angles were developed from an early date. Here and throughout the present document, the viewing angle of an endoscope is always understood to mean the direction looking outward from the distal end of the endoscope, that is, the direction in which an object is situated that appears in the center of the image recorded by means of the endoscope. With many applications, however, a fixed viewing angle is a disadvantage. In the most unfortunate case, the endoscope must be replaced repeatedly during a medical procedure. In such cases it is advantageous to use an endoscope with a viewing angle that can be adjusted and/or modified in situ.

Observing an object in a cavity by means of an endoscope assumes as a rule that there is an illumination of the object. For this purpose an endoscope comprises, for example, lightwave conductors, in particular fiber optic cables, by means of which illuminating light is transmitted from the proximal end of the endoscope along the shaft to the distal end of the endoscope. Light outlet surfaces of the lightwave conductors on the distal end of the endoscope are positioned and configured in such a way that the entire field of vision or visual field is sufficiently illuminated.

In an endoscope with adjustable viewing angle, the illuminating light at the distal end of the endoscope is distributed in the simplest case in such a way that the entire visual field is illuminated, independently of the particular viewing angle selected. However, this can lead to a series of disadvantages. In particular, light capacity is wasted because, independently of the viewing angle that is in fact selected, all visual fields of all viewing angles are constantly selected. Thus, for a predetermined desired brightness, it is necessary to have a markedly higher light capacity available altogether than is needed with an endoscope with fixed viewing angle.

Another disadvantage derives from the fact that high-intensity illuminating light can photothermally or photochemically damage tissues or other objects. In an endoscope with fixed viewing angle, as a rule there is clearly too small a distance from the distal end of the endoscope to an object, at least in observing the acquired image. When a video camera is used on the endoscope, an automatic warning of users is also possible if the brightness of a captured image exceeds a predetermined threshold. However, in an endoscope with adjustable viewing angle, part of the illuminating light falls on objects lying outside the visual field. This avoids an undesired proximity of the distal end of the endoscope to these objects, and a resulting exposure of these objects to an excessive radiant power.

Another disadvantage is the fact that illuminating light that is at first radiated outside the visual field can be dispersed or reflected by objects or opaque media. The reflected or dispersed illuminating light can arrive directly or indirectly in the observation beam path. Consequently, contrasts and, especially in dark image areas, the distinguishability of objects can be reduced.

Yet another disadvantage arises from the fact that the degree of illumination or intensity of the illuminating light is essentially constant in the direction in which the viewing angle can be varied (often also called the vertical direction), while in the direction perpendicular thereto (often also called the horizontal direction), as a rule it decreases slightly toward the edge of the visual field. However, from endoscopes with fixed viewing angle, users as a rule are accustomed to a degree of illumination that slightly decreases toward the edge of the visual field both in the horizontal and in the vertical direction. A constant degree of illumination in the vertical direction can therefore be experienced as irritating.

Patent DE 600 15 375 T2 describes an arrangement of several prisms. One of the prisms can rotate around an axis in order to cast illuminating light at an adjustable viewing angle. The prisms, however, take up space that is no longer available with constantly smaller shaft cross-sections.

SUMMARY OF THE INVENTION

It is an object of the present invention to provide an improved endoscope with respect to its illumination, with adjustable viewing angle and an improved method for illuminating an adjustable visual field.

This object is achieved through the contents of the independent claims.

Refinements are indicated in the dependent claims.

Embodiments of the present invention are based on the idea of switching illuminating light for several different viewing angles, by means of a light splitting device, into several different lightwave conductors by which the illuminating light is transmitted to several different light outlet devices, which radiate the illuminating light to different solid angles. The light splitting device can be positioned on the proximal end of the endoscope, where as a rule there is markedly more structural space available than at the distal end of the endoscope.

An endoscope with adjustable viewing angle includes a number of light outlet devices on the distal end of the endoscope, such that the light outlet devices are configured and positioned to direct illuminating light emerging from various light outlet devices to solid angles differing at least in part; several lightwave conductors to direct illuminating light to the light outlet devices; and a light splitting device for controllable switching of illuminating light into one or more of the number of lightwave conductors.

The viewing angle of the endoscope can pivot in particular around a pivot axis that is perpendicular to the longitudinal axis of the endoscope. For the viewing angle to be capable of pivoting, a pivotable prism or a pivotable mirror, for example, is provided in the observation beam path of the endoscope.

Every lightwave conductor includes, for example, a glass or plastic fiber or a bundle of glass or plastic fibers. The fiber or fibers can be single-mode or multimode fibers. Alternatively, each lightwave conductor includes one or more liquid light conductors. The light inlet surfaces of the lightwave conductors are positioned in particular on the proximal end of the endoscope. Precisely one light outlet device, in particular, is associated with each lightwave conductor.

The light outlet devices include, in particular, light outlet surfaces at distal ends of the lightwave conductors. If the lightwave conductors include glass or plastic fibers, their distal ends can be joined in openings on the distal end of the endoscope, for example by means of a cement. The light outlet devices here are constituted by light outlet surfaces, which arise after the hardening of the cement through grinding and polishing of the originally protruding ends of the fibers.

Alternatively, the light outlet devices comprise, for example, lenses and/or glass coverings. Independently of the configuration of the light outlet devices, precisely one lightwave conductor or one group of lightwave conductors, for instance a bundle of glass fibers, can be associated with each light outlet device.

The endoscope described here, with several light outlet devices, lightwave conductors to conduct illuminating light to the light outlet devices and a light splitting device for controllable switching of illuminating light into the lightwave conductors, makes it possible to illuminate or light up only the visual field in the momentarily selected viewing angle. The radiant capacity that is diverted into solid angles, and that lies outside the momentary visual field, is at least strongly reduced thereby. This reduces the required total radiant capacity, the risk of photothermal or photochemical injuries and the intensity of scattered light that reduces the image contrast. In addition, with corresponding configuration of the light outlet devices and light splitting device, it is possible to achieve a distribution of the illuminating light that is experienced as pleasant by the users and at which the illuminating intensity slightly decreases toward all borders of the visual field.

The use of lightwave conductors between the light splitting device and the light outlet devices allows an enlarged free space in the structure. In particular, the light splitting device can be positioned at a considerable distance from the distal end of the endoscope, for example at the proximal end of the endoscope where as a rule there is more structural space available. The lightwave conductors and light outlet devices take up only very little space and can therefore be fitted even into endoscopes with very small cross-sections. This applies in particular to light outlet devices in the form of simple distal light outlet surfaces of the lightwave conductors.

By means of a simple mechanical device, or else by means of an electrical or magnetic apparatus, the light splitting device can be controlled in such a way that the endoscope is switched into other lightwave conductors, simultaneously with a modification of the viewing angle of the endoscope, in order to adjust the illuminating solid angle in each case to the momentary visual field. Operating devices for controlling or adjusting the viewing angle are typically positioned on the proximal end of the endoscope. Every adjustment made to an operating device can therefore be transmitted directly to a light splitting device likewise positioned on the proximal end of the endoscope.

With an endoscope as described here, the light splitting device can include a prism that is movable into several positions, such that at various positions of the prism, illuminating light can be switched into different lightwave conductors.

The prism, in particular, is continually movable or can be moved into positions or assume positions that form a continuum. Alternatively, for example by means of mechanical catch-lock devices, it is possible to predetermine discrete positions that the prism can assume.

The prism, in particular, can pivot or rotate around an axis, such that the illuminating light that is provided falls onto the prism essentially parallel to this axis. By means of a rotation of the prism, the direction of the illuminating light diverted by the prism can by varied, in particular on a conical mantle. In the simplest case, the light inlet surfaces or the proximal ends of the lightwave conductors lie on this conical mantle.

In an endoscope as described here, the light splitting device can include a rotatable pair of prisms rigidly connected with one another.

The pair of prisms rigidly linked to one another are, in particular, connected by means of a transparent cement. The refractive indices of the materials of the two prisms can comprise a wavelength dependence acting in opposite directions, in order to reduce or suppress wavelength dependence of the diversion of the illuminating light by the prism pair.

The light inlet surface and the light outlet surface of the pair of rigidly interconnected prisms, in particular, are parallel to one another. This can simplify precise guidance of the rotatable pair of prisms. In particular in the case of parallel light inlet and outlet surfaces of the prism pair, the two prisms comprise materials with different refractive indices.

In an endoscope as described here, the light splitting device can include two pairs of prisms that can rotate with respect to one another.

The prisms of a pair comprise different refractive indices and can be rigidly connected with one another, in particular by cementing. In the case of two independently rotatable prism pairs, a light beam falling on the light splitting device can be diverted as desired in two dimensions inside predetermined boundaries. Illuminating light can thus be directed, for example, onto light inlet surfaces of lightwave conductors that are arranged in an array.

If both prism pairs rotate in opposite directions to one another, illuminating light that falls on the light splitting device can be directed, for example, onto light inlet surfaces that are arranged along a straight or other curve in order to switch the illuminating light into the light inlet surfaces. For contrary rotation of the prism pairs, these are mechanically coupled with one another by a corresponding gear unit.

The described light splitting device with one or more prisms interconnected individually or in pairs forms a light splitting device that is simple, robust and not sensitive with respect to faulty adjustment and that can be produced inside a small structural space.

In an endoscope as described here, the light splitting device can include two non-mixable fluids with different refractive indices and a border surface control device for electrical or magnetic modification of at least either the arrangement or the shape of a border surface between the non-mixable fluids.

The described arrangement of two non-mixable fluids with different refractive indices is also designated as a fluid lens. By modifying the curvature of the border surface between the non-mixable fluids with different refractive indices, the refractive force or the focal length of the liquid lens can be modified. By tipping a border surface that is essentially level between non-mixable fluids with different refractive indices, the two fluids act as a prism with variable diversion. Thus, illuminating light that has been provided can be diverted onto one or more light inlet surfaces of lightwave conductors in order to switch the illuminating light into the lightwave conductor or conductors. By a variation of the curvature of the border surface between the non-mixable fluids, the number of light inlet surfaces onto which the illuminating light is simultaneously diverted can be modified. The described light splitting device with two non-mixable fluids allows in this manner a very quick and flexible control of the switching of illuminating light into one or more of the number of lightwave conductors.

In an endoscope in which the light splitting device includes two non-mixable fluids and a border surface control device, the border surface control device can include several electrodes, such that the fluids are configured and the electrodes are configured and arranged in such a way that by applying an electrostatic current to the electrodes, the border surface between the non-mixable fluids can be at least either moved or deformed.

Because of the electrostatic moving and/or deformation of the border surface between the non-mixable fluids with different refractive indices, illuminating light can be switched into different lightwave conductors. It is a prerequisite that at least one of the two non-mixable fluids can be influenced by electrostatic fields, in particular attracted or repelled. Alternatively, at least one of the two non-mixable fluids can be influenced by a magnetic field, and the border surface control device includes one or more electromagnets or one or more movable permanent magnets.

In an endoscope as described here, the light splitting device can include a reflecting surface, movable into several positions, for diverting illuminating light, such that with different positions of the reflecting surface, illuminating light can be switched into different lightwave conductors.

The reflecting surface is, in particular, continually movable or movable into every position of a continuum of positions. The reflecting surface is, in particular, translationally or rotationally movable. The reflecting surface is, for example, a mirrored or totally reflecting surface of a mirror or of a prism and/or of a transparent body. Sliding or rotating and/or pivoting a reflecting surface allows in simple manner a diverting of the illuminating light onto one or more selected light inlet surfaces of lightwave conductors.

In an endoscope as described here, the light inlet surfaces of the lightwave conductors and the light splitting device in particular are positioned on the proximal end of the endoscope.

As already mentioned, the use of lightwave conductors makes possible a great freedom of configuration and in particular an almost completely free choice in arranging the light splitting device. Arranging the light splitting device on the proximal end of the endoscope allows a configuration of the shaft of the endoscope with very small cross-section without requiring the light splitting device to be produced in especially small size.

As already mentioned, arranging the light splitting device on the proximal end of the endoscope has the further advantage that the distance between the light emitting device and operating devices likewise positioned on the proximal end of the endoscope can be small. The light emitting device can thus be controlled immediately and precisely, with low construction cost.

In a method for illuminating a visual field in an adjustable viewing angle of an endoscope, illuminating light is provided and the provided illuminating light is switched into one or more lightwave conductors associated with a momentarily selected viewing angle, from a number of lightwave conductors. The switched-in illuminating light is transmitted by means of the selected lightwave conductor or conductors to one or more associated light outlet devices on the distal end of the endoscope. The illuminating light transmitted by means of a light wave conductor is diverted into a solid angle corresponding to the visual field by means of a light outlet device associated with the lightwave conductor.

A method as described here can be performed in particular with an endoscope, as described here.

In a method as described here, in addition a chosen viewing angle of the endoscope and a light splitting device corresponding to the selected viewing angle of the endoscope can be selected.

BRIEF DESCRIPTION OF THE DRAWINGS

Hereinafter, embodiments are described more closely with reference to the appended drawings, which are as follows:

FIG. 9 shows a schematic flow diagram.

DETAILED DESCRIPTION OF THE INVENTION

Figure 1:
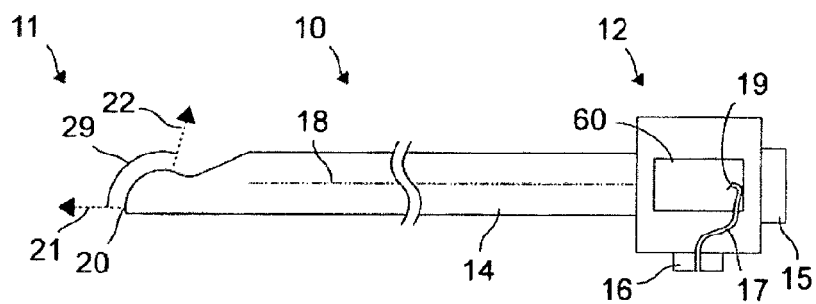
FIG. 1 shows a schematic depiction of an endoscope with adjustable viewing angle.

FIG. 1 shows a schematic depiction of an endoscope 10 with a distal end 11, a proximal end 12 and a rigid shaft 14 that extends from the distal end 11 to the proximal end 12. Alternatively, the shaft 14 can be flexible or partly flexible. The cross-section of the shaft 14 or at least the outer contour of the cross-section of the shaft 14 is constant or essentially constant between the distal end 11 and the proximal end 12. In particular, the contour of the cross-section of the shaft 14 is circular or elliptical. In this case the longitudinal axis 18 of the endoscope 10 shown in FIG. 1 is the axis of symmetry of the mantle surface of the shaft 14 between the distal end 11 and the proximal end 12. In a cylindrical mantle surface of the shaft 14, the longitudinal axis 18 is also the set of the center points or centroids of the cross-section of the shaft 14 between the distal end 11 and the proximal end 12. In a cylindrical mantle surface of the shaft 14, the longitudinal axis 18 is also the axis of symmetry of the mantle surface.

On the distal end 11, the shape of the shaft 14 departs from cylindrical symmetry, as is shown by way of example in FIG. 1. In particular, the shaft 14 comprises on the distal end 11 an opening that is closed by a transparent window component with a vaulted surface 20. In particular, the window component with the vaulted surface 20 closes the opening with a hermetical insulation. The surface 20 of the window component has the shape, for example, of a segment of a cylindrical mantle, such that the axis of symmetry of the cylinder is perpendicular to the longitudinal axis 18 of the endoscope 10 and to the plane of projection of FIG. 1. Alternatively, the surface 20 of the transparent window component has the shape of a segment of a spherical surface or of a rotationally symmetrical or non-rotationally symmetrical ellipsoid.

On the distal end 11 of the endoscope 10, optical devices are positioned in the shaft 14 that are not shown in FIG. 1 and that make possible a variation of the viewing angle of the endoscope between a first extreme viewing angle 21 and a second extreme viewing angle 22. The viewing angle is pivotable between the two extreme viewing angles 21, 22, in particular around a pivot axis that is perpendicular to the plane of projection of FIG. 1. The viewing angle in each case is the direction based on the distal end 11 of the endoscope 10 in which an object is situated that appears in the center of an image recorded by the endoscope 10.

In the example illustrated in FIG. 1, the first extreme viewing angle 21 is parallel or essentially parallel to the longitudinal axis 18 of the endoscope 10. Between the extreme viewing angles 21, 24 there lies a solid angle 29, which in the illustrated example spans about 120 degrees. Within this solid angle, the viewing angle of the endoscope 10 is, in particular, continually displaceable.

On the proximal end 12 the endoscope 10 comprises a first coupling 15 for optical coupling of the endoscope 10 with a video camera or an eyepiece as well as a second coupling 16 for coupling the endoscope 10 with a light source via a light conductor cable. Inside the shaft 14 a number of lightwave conductors are positioned, which are described hereinafter with reference to FIG. 2. A short lightwave conductor 17 couples the second coupling 16 with a light splitting device 60, such that a light outlet surface 19 is positioned on the light splitting device 60.

Figure 2:
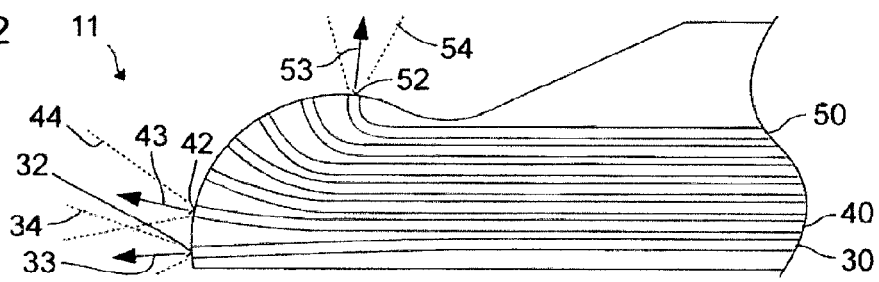
FIG. 2 shows a schematic depiction of the distal end of the endoscope from FIG. 1.

FIG. 2 shows a schematic enlarged view of the distal end 11 of the endoscope 10 presented above with reference to FIG. 1. Shown here, similarly as in a sectional drawing, are several lightwave conductors 30, 40, 50 that run in the interior of the shaft 14. To avoid cluttering the drawing, only three of the lightwave conductors are provided with reference numbers.

Each of the lightwave conductors 30, 40, 50 ends in a light outlet surface 32, 42, 52 close to the window component that is described above in connection with FIG. 1 and that is not shown in FIG. 2. The light outlet surfaces 32, 42, 52 are formed, for example, by the ends of the lightwave conductors 30, 40, 50 being inserted into corresponding openings of the housing of the shaft 14 with a protrusion and by means of a cement, and then ground and polished back to the contour of the housing of the shaft 14. Each lightwave conductor 30, 40, 50 consists, in particular, of a bundle of glass or plastic fibers. The light outlet surfaces 32, 42, 52 form simple light outlet devices. Alternatively, lenses, covering glasses and/or other light outlet devices can be provided.

Central radiant directions 33, 43, 53 of the light outlet surfaces 32, 42, 52 are, in particular, defined directly on the light outlet surfaces 32, 42, 52 by the directions of the lightwave conductors 30, 40 50. The central radiant directions 33, 43, 53 correspond in particular essentially to the surface normals of the light outlet surfaces 32, 42, 52.

Illuminating light emerging from a light outlet surface 32, 42, 52, however, spreads out not only in the central radiant direction but also inside a light cone 34, 44, 54. The intensity or radiant capacity declines in moving outward from the central radiant direction 33, 43, 53 and/or with an increasing angle to the central radiant direction. The light cones 34, 44, 54 indicated in FIG. 2 are, for example, the solid angles inside which the intensity or radiant capacity of the illuminating light emerging from a light outlet surface 32, 42, 52 equals at least half of the maximum value. The distribution or angle dependency of the radiant capacity of the illuminating light emerging from a light outlet surface 32, 42, 52 is determined in particular by the switching into the proximal ends of the lightwave conductors 30, 40, 50, not shown in FIG. 2, because of the transmission properties of the lightwave conductors 30, 40, 50.

In the example depicted in FIG. 2, the light cones 34, 44, 54 emerging from different light outlet surfaces 32, 42, 52 overlap. Therefore, areas exist in which objects are illuminated by illuminating light that emerges from two or more different light outlet surfaces 32, 42, 52, with radiant capacity that is not just inconsequential.

Alongside or between the light outlet surfaces 32, 42, 52 of the lightwave conductors 30, 40, 50, additional light outlet surfaces are constituted by additional lightwave conductors that in FIGS. 2 through 8 are not provided with reference numbers. The number of lightwave conductors provided in the endoscope 10 and their arrangement can differ from those shown in FIG. 2.

FIGS. 3 through 8 show schematic depictions of several different embodiments of the proximal end 12 of the endoscope described above with reference to FIGS. 1 and 2. FIGS. 3 through 8, in the manner of sectional depictions, each show devices positioned in the interior of the endoscope.

Figure 3:
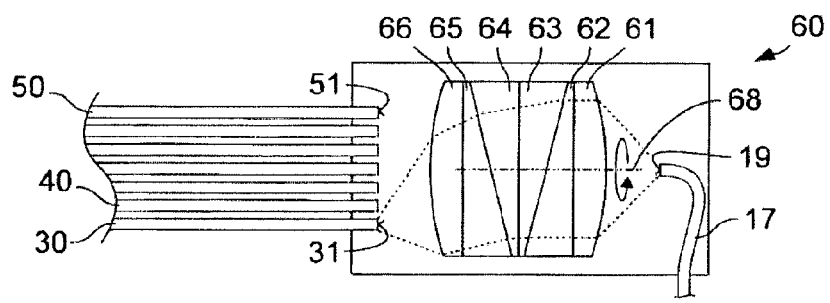
FIG. 3 shows a schematic depiction of an embodiment of the proximal end of the endoscope from FIGS. 1 and 2.
Figure 4:
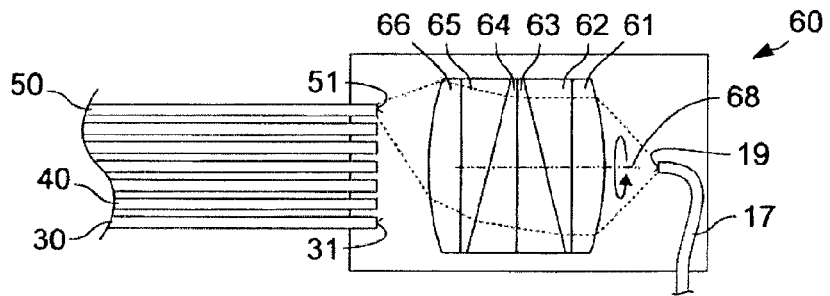
FIG. 4 shows another schematic depiction of the embodiment from FIG. 3.

FIGS. 3 and 4 show schematic depictions of an embodiment of the endoscope 10 described above with reference to FIGS. 1 and 2, in which the light splitting device 60 is a rotation prism device. The rotation prism device 60 includes a light inlet lens 61, a first prism 62, a second prism 63, a third prism 64, a fourth prism 65 and a light outlet lens 66.

The light outlet surface 19 of the short proximal lightwave conductor 17 is positioned at the focal point of the light inlet lens 61. One light outlet side of the light outlet lens 61, facing the first prism 62, is positioned level and parallel to a light inlet surface of the first prism 62.

The first prism 62 and the second prism 63 are joined together, in particular by means of a transparent cement. One light inlet surface of the first prism 62, facing the light inlet lens 61, and a light outlet surface of the second prism 63, facing the third prism 64, are level and parallel to one another. The first prism 62 and the second prism 63 can rotate together around an axis 68.

The third prism 64 and the fourth prism 65 are joined together, in particular by means of a transparent cement. One light inlet surface of the third prism 64, facing the second prism 63, and one light outlet surface of the fourth prism 65, facing the light outlet lens 66, are level and parallel to one another. The third prism 64 and the fourth prism 65 can rotate together around the axis 68.

A light inlet surface of the light outlet lens 66, facing the fourth prism 65, is level. The light inlet surfaces 31, 51 of the lightwave conductors 30, 40, 50 are positioned in a focal surface, in particular in a focal plane of the light outlet lens 66 of the rotation prism device 60.

The first prism 62 and second prism 63 comprise transparent materials, in particular glasses, with varying refractive indices. The third prism 64 and fourth prism 65 comprise transparent materials, in particular glasses, with different refractive indices. The first prism 62 and fourth prism 65 can comprise the same material, and likewise the second prism 63 and third prism 64 can comprise the same material.

The first prism 62 and second prism 63 on the one hand, as well as the third prism 64 and fourth prism 65 on the other hand, can rotate independently of one another around the rotation axis 68. Alternatively, the first prism 62 and second prism 63 on the one hand, as well as the third prism 64 and fourth prism 65 on the other hand, can be coupled together, for example mechanically, in such a way that they are constantly counter-rotated.

The light outlet surface 19 of the short proximal lightwave conductor 17 is positioned at the focal point of the light inlet lens 61. The light inlet lens 61 has a collimating effect, so that illuminating light emerging from the light outlet surface 19 of the short proximal lightwave conductor 17 spreads parallel or essentially parallel within the prisms 62, 63, 64, 65.

The light inlet surfaces 31, 51 of the lightwave conductors 30, 40, 50 are positioned on the focal surface of the light outlet lens 66. The illuminating light collimated by the light inlet lens 61 is bundled, in particular focused, by the light outlet lens 66 onto one or a few light inlet surfaces 31, 51 of the lightwave conductors 30, 40, 50.

Because the border surface between the first prism 62 and the second prism 63 as well as the border surface between the third prism 64 and the fourth prism 65 is not perpendicular to the spreading direction of the collimated illuminating light, refraction occurs on each of these border surfaces. The direction in which the light spreads is modified by the refraction at the two border surfaces, within a plane in each case that is defined by the light's spreading direction and the surface normal of the border surface. By rotation of the first prism 62 and of the second prism 63 and/or by rotation of the third prism 64 and fourth prism 65 around the axis of rotation 68, the surface normal of the border surface between the first prism 62 and the second prism 63 and the surface normal of the border surface between the third prism 64 and the fourth prism 65 rotate on a conical mantle around the axis of rotation 68. Thus it is possible to select the changes of direction on both border surfaces by rotation of the first prism 62 and second prism 63 and/or by rotation of the third prism 64 and fourth prism 65 around the axis of rotation 68.

For example, FIGS. 3 and 4 depict two different positions of the first prism 62 and second prism 63 and simultaneously two different positions of the third prism 64 and fourth prism 65. In the positions of the first prism 62 and second prism 63 or of the third prism 64 and fourth prism 65 as illustrated in FIG. 3, illuminating light emerging from the light outlet surface 19 is switched into the light inlet surface 31 of the first lightwave conductor 30. In the position of the prisms 62, 63, 64, 65 shown in FIG. 3, illuminating light is thus transmitted to the distal end 11 of the endoscope 10 by means of the first lightwave conductor 30. The light cone 34 emerging from the light outlet surface 32 of the first lightwave conductor 30, as shown in FIG. 2, is thereby generated.

In the positions of the first prism 62 and second prism 63 or of the third prism 64 and fourth prism 65 as shown in FIG. 4, illuminating light emerging from the light outlet surface 19 of the short proximal lightwave conductor 17 is switched into the light inlet surface 51 of the third lightwave conductor 50. In the position of the prisms 62, 63, 64, 65 shown in FIG. 4, illuminating light is transmitted to the distal end 11 of the endoscope 10 by means of the third lightwave conductor 50. The light cone 54 emerging from the light outlet surface 52 of the third lightwave conductor 50, as shown in FIG. 2, is thereby generated.

In an independent rotation of the first prism 62 and second prism 63 on the one hand, and of the third prism 64 and fourth prism 65 on the other hand, illuminating light emerging from the light outlet surface 19 of the short proximal lightwave conductor 17 can be bundled onto light inlet surfaces 31, 51 of lightwave conductors 30, 40, 50, positioned in a two-dimensional array, and can be switched into them.

If the first prism 62 and second prism 63 on the one hand, and the third prism 64 and fourth prism 65 on the other hand, are coupled together in such a way that they can only rotate contrary to one another, illuminating light emerging from the light outlet surface 19 of the short proximal lightwave conductor 17 can be bundled onto light inlet surfaces 31, 51 of lightwave conductors 30, 40, 50, which are positioned along a line, in particular a straight line, and can be switched into them.

Figure 5:
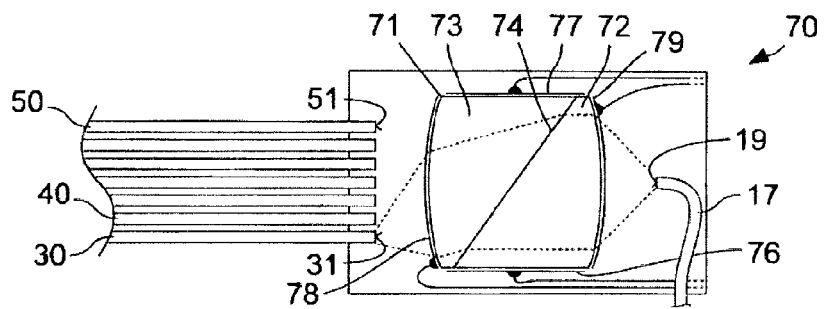
FIG. 5 shows a schematic depiction of an additional embodiment of the proximal end of the endoscope from FIGS. 1 and 2.
Figure 6:
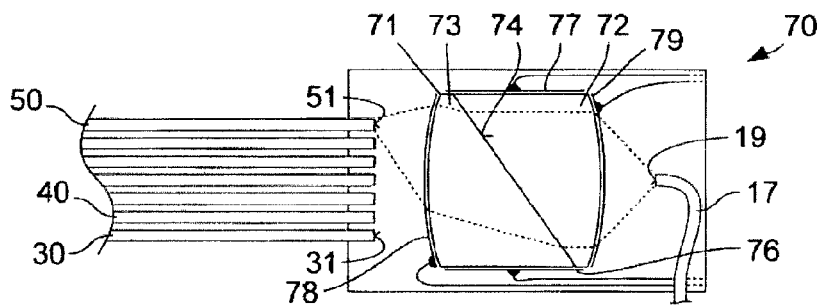
FIG. 6 shows an additional schematic depiction of the embodiment from FIG. 5.

FIGS. 5 and 6 show schematic depictions of an additional embodiment of the endoscope 10 described above with reference to FIGS. 1 and 2. In this embodiment, instead of the rotation prism device 60 presented above with reference to FIGS. 3 and 4, a fluid lens device 70 is provided as light splitting device. Said fluid lens device 70 includes a hollow body 71 in which a first fluid 72 and a second fluid 73 are placed. The first fluid 72 and second fluid 73 comprise different refractive indices and are not mixable. For example, the first fluid 72 can be hydrophilic or lipophobic and the second fluid 73 lipophilic or hydrophobic. Between the first fluid 72 and second fluid 73, a border surface 74 is configured, which is level in each of the examples shown in FIGS. 5 and 6.

A first electrode 76, a second electrode 77, a third electrode 78 and a fourth electrode 79 are positioned on the transparent hollow body 51. Additional electrodes, which are not shown in FIGS. 5 and 6, can be positioned, for example, in front of or behind the plane of projection of FIGS. 5 and 6. At least the side of the hollow body 71 facing the light outlet surface 19 of the short proximal lightwave conductor 17 and the side of the hollow body 71 facing the light inlet surfaces 31, 51 of the lightwave conductors 30, 40, 50, as well as the electrodes 78, 79 positioned on these two sides of the hollow body 71, are transparent in order to allow transmission of illuminating light.

The side facing the light outlet surface 19 of the short proximal lightwave conductor 17 and the side facing the light inlet surfaces 31, 51 of the lightwave conductors 30, 40, 50, as indicated in FIGS. 5 and 6, are vaulted in order to collimate or to focus illuminating light. In particular, the light outlet surface 19 of the short proximal lightwave conductor 17 and the light inlet side of the hollow body 71 facing the light outlet surface 19 are positioned, and the light inlet side is vaulted, in such a way that illuminating light emerging from the light outlet surface 19 of the short proximal lightwave conductor 17 spreads parallel inside the hollow body 71 and the fluids 72, 73. The light inlet surfaces 31, 51 of the lightwave conductors 30, 40, 50 and the light outlet side of the hollow body 71 facing the light inlet surfaces 31, 51 are positioned, and the latter is vaulted, in such a way that illuminating light spreading parallel inside the hollow body 71 and the fluids 72, 73 is bundled or focused on one or a few light inlet surfaces 31, 51.

At least either the first fluid 72 or the second fluid 73 is configured in such a way that it interacts with an electric field. On applying electrostatic current to the electrodes 75, 76, 77, 78, the border surface 74 can thus be geometrically modified. In particular, the border surface 74 can be brought into different tipped arrangements or positions, which are indicated in FIGS. 5 and 6, and in which the border surface 74 is level in each case. Contrary to the depictions in FIGS. 5 and 6, the border surface 74 can be further curved between the first fluid 72 and the second fluid 73. Because of a curvature of the border surface 74 between the first fluid 72 and the second fluid 73, the bundling or focusing of the illuminating light emerging from the light outlet surface 19 of the short proximal lightwave conductor 17 can be modified; in particular, the number of light inlet surfaces 31, 51 into which the illuminating light is simultaneously switched, can be modified.

In the arrangement of the border surface 74 shown in FIG. 5, illuminating light is transmitted to the distal end 11 of the endoscope 10 by means of the first lightwave conductor 30. The light cone 34 emerging from the light outlet surface 32 of the first lightwave conductor 30, as show in FIG. 2, is thereby generated.

In the arrangement of the border surface 74 shown in FIG. 6, illuminating light is transmitted to the distal end 11 of the endoscope 10 by means of the third lightwave conductor 50. The light cone 54 emerging from the light outlet surface 52 of the third lightwave conductor 50, as shown in FIG. 2, is thereby generated.

In additional arrangements of the border surface 74 between the arrangements indicated in FIGS. 5 and 6, illuminating light emerging from the light outlet surface 19 of the short proximal light wave conductor 17 is bundled onto one or more of the light inlet surfaces between the light inlet surface 31 of the first lightwave conductor 30 and the light inlet surface 51 of the third lightwave conductor 50, or is switched into them.

Figure 7:
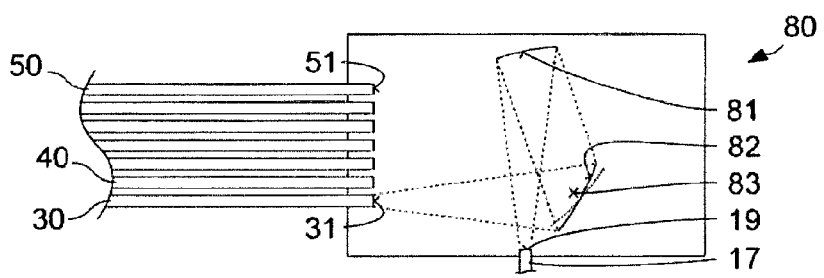
FIG. 7 shows a schematic depiction of an additional embodiment of the proximal end of the endoscope from FIGS. 1 and 2.
Figure 8:
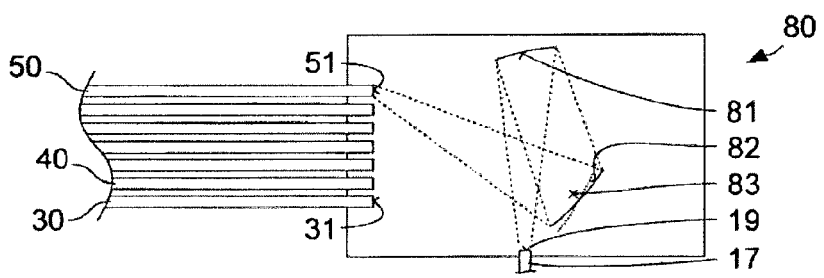
FIG. 8 shows an additional schematic depiction of the embodiment from FIG. 7.

FIGS. 7 and 8 show schematic depictions of an additional embodiment of the proximal end 12 of the endoscope 10 described above with reference to FIGS. 1 and 2. In this embodiment, instead of the rotation prism device 60 introduced above with reference to FIGS. 3 and 4 or the fluid lens device 70 presented above with respect to FIGS. 5 and 6, a pivot mirror device 80 is provided as light splitting device. The pivot mirror device 80 includes a first reflecting surface 81 and a second reflecting surface 82. Each of the two reflecting surface 81, 82 is, for example, a reflecting surface of a mirror or a mirrored or totally reflecting surface of a prism or other transparent body.

At least either the first reflecting surface 81 or the second reflecting surface 82 is of convex curvature, such that in the examples illustrated in FIGS. 7 and 8 both reflecting surfaces 81, 82 are of convex curvature. Illuminating light emerging from the light outlet surface 19 of the short proximal lightwave conductor 17 is successively reflected, first by the first reflecting surface 81 and then by the second reflecting surface 82, and bundled or focused onto one or a few light inlet surfaces 31, 51 of the lightwave conductors 30, 40, 50 and switched into them. In particular, the first reflecting surface 81 and the second reflecting surface 82 are configured and positioned in such a way that illuminating light emerging from the light outlet surface 19 of the short proximal lightwave conductor 17 spreads parallel between the first reflecting surface 81 and the second reflecting surface 82. The first reflecting surface 81 thus has a collimating effect. For this purpose, in particular the light outlet surface 19 of the short proximal lightwave conductor 17 is positioned at a focus of the first reflecting surface 81.

At least either the first reflecting surface 81 or the second reflecting surface 82, in addition, can pivot around an axis. In the example illustrated in FIGS. 7 and 8, the second reflecting surface 82 can pivot around an axis 83, which is essentially perpendicular to the plane of projection of FIG. 7. By pivoting the second reflecting surface 82 around the pivot axis 83, it is possible to select on which of the light inlet surfaces 31, 51 of the lightwave conductors 30, 40, 50 illuminating light is bundled or focused that emerges from the light outlet surface 19 of the short proximal lightwave conductor 17.

In the position of the second reflecting surface 82 shown in FIG. 7, illuminating light emerging from the light outlet surface 19 of the short proximal lightwave conductor 17 is bundled by the reflecting surfaces 81, 82 onto the light inlet surface 31 of the first lightwave conductor 30 or is switched into it. In the position of the second reflecting surface 82 shown in FIG. 7, illuminating light is thus transmitted to the distal end 11 of the endoscope 10 by means of the first lightwave conductor 30. The light cone 34 shown in FIG. 2 and emerging from the light outlet surface 32 of the first lightwave conductor 30 is thereby generated.

In the position of the second reflecting surface 82 as shown in FIG. 8, illuminating light emerging from the light outlet surface 19 of the short proximal lightwave conductor 17 is bundled by the reflecting surfaces 81, 82 onto the light inlet surface 51 of the third lightwave conductor 50, or is switched into it. In the position of the second reflecting surface 82, as shown in FIG. 8, illuminating light is thus transmitted to the distal end 11 of the endoscope 10 by means of the third lightwave conductor 50. The light cone 54 shown in FIG. 2 and emerging from the light outlet surface 52 of the third lightwave conductor 40 is thereby generated.

In further positions of the second reflecting surface 82 between the positions depicted in FIGS. 7 and 8, illuminating light emerging from the light outlet surface 19 of the short proximal lightwave conductor 17 is bundled onto one or more of the light inlet surfaces between the light inlet surface 31 of the first lightwave conductor 30 and the light inlet surface 51 of the third lightwave conductor 50 or is switched into it.

In FIG. 2 the light outlet surfaces 32, 42, 52 of the lightwave conductors 30, 40, 50 are positioned by way of example in such a way that equal or essentially equal angles are situated between the central radiant directions 33, 43, 53 of neighboring light outlet surfaces 32, 42, 52 in each case. Light outlet surfaces 32, 42, 52 can be positioned along two opposite edges of the window component of the observation beam path. In this case the light outlet surfaces 32, 42, 52 can be positioned so that the central radiant directions 33, 43, 53 of the light outlet surfaces are displaced with respect to one another. For example, the central radiant directions 33, 43, 53 of the light outlet surfaces on one side of the window component form angles of −10 degrees, +10 degrees, +30 degrees, +50 degrees, +70 degrees, +90 degrees and +110 degrees to the longitudinal axis 18 of the endoscope, and the central radiant directions 33, 43, 53 of the light outlet surfaces on the opposite side of the window component form angles of 0 degrees, +20 degrees, +40 degrees, +60 degrees, +80 degrees, +100 degrees and +120 degrees to the longitudinal axis 18 of the endoscope.

In particular in the last-mentioned example of the arrangement of the light outlet surface 32, 42, 52, as well as with other arrangements of the light outlet surfaces 32, 42, 52, the light inlet surfaces 31, 51 of the lightwave conductors 30, 40, 50 can be arranged differently from those illustrated in FIGS. 3 through 8. In FIGS. 3 through 8 the light inlet surfaces 31, 41, 51 are positioned at equal mutual distances by way of example. Contrary thereto, it can be advantageous, depending on the arrangement of the light outlet surfaces 32, 42, 52 on the distal end 11 of the endoscope 10, to arrange the light inlet surfaces 31, 41, 51 differently, for example grouped in pairs.

In addition, contrary to the illustrations in FIGS. 3 through 8, cones or tapering shapes, in particular fiber cones or full cones, can be provided on the light inlet surfaces 31, 41, 51 of the lightwave conductors 30, 40, 50. By means of a cone of this type, the angle distribution of the illuminating light switched into a lightwave conductor can be modified or adjusted. On the basis of the transmission properties of the lightwave conductors 30, 40, 50, the opening angles of the light cone 34, 44, 45 emerging from the light outlet surfaces 32, 42, 52 of the lightwave conductors 30, 40, 50 can be selected in this way.

FIG. 9 shows a schematic flow diagram of a method for illuminating a visual field in an adjustable viewing angle of an endoscope. Although this method can also be executed by means of an endoscope that differs from the endoscopes described above with reference to FIGS. 1 through 8, hereinafter reference numbers from FIGS. 1 through 8 are used by way of example for the sake of clarity.

In a first step 101, illuminating light is provided. The illuminating light is, for example, provided from a light source that is coupled with the endoscope 10 by a light conductor cable and a coupling 16 of the endoscope 10. Alternatively the illuminating light is generated from a light source integrated into the endoscope 10.

In a second step 102, a viewing angle 21, 22 of the endoscope 10 is selected. For this purpose, a prism or a mirror, for example, is pivoted on the distal end 11 of the endoscope 10.

In a third step 103, a light splitting device 60; 70; 80 is selected corresponding to the selected viewing angle 21, 22 of the endoscope 10. In a fourth step 104, the illuminating light that has been provided is switched by means of the light splitting device 60; 70; 80 selected in the third step 103 into one or more lightwave conductors 30, 40, 50 associated with a momentarily selected viewing direction 21, 22, out of a number of lightwave conductors 30, 40, 50.

In a fifth step 105, the illuminating light that has been switched in in the fourth step 104 is transmitted to one or more associated light outlet devices 32, 42, 52 on the distal end 11 of the endoscope 10 by means of the lightwave conductor or conductors, into which the illuminating light was switched in the fourth step 104. In a sixth step 106, the illuminating light transmitted in the fifth step 105 by means of a lightwave conductor is diverted into a solid angle 34, 44, 54 corresponding to the visual field by means of one of the light outlet devices 32, 42, 52 associated with the lightwave conductor.

The invention claimed is:

1. An endoscope with adjustable viewing angle, the endoscope comprising:
   a plurality of light outlet devices on a distal end of an endoscope, the plurality of light outlet devices positioned in order to direct illuminating light emerging from different light outlet devices into at least partly different solid angles;
   a plurality of lightwave conductors for directing illuminating light to the plurality of light outlet devices; and
   a light splitting device positioned on the proximal end of the endoscope, the light splitting device having a first prism and a second prism, the first and second prism rotating about an axis extending from the proximal end of the endoscope to the distal end of the endoscope for controllably focusing illuminating light into one or more of the plurality of lightwave conductors;
   wherein the first and second prisms are rigidly connected with one another.

2. The endoscope of claim 1, wherein the light splitting device further includes a third prism and a fourth prism that can rotate with respect to the first and second prisms about the axis.

3. The endoscope of claim 2, wherein the third prism and the fourth prism are joined together by cement.

4. The endoscope of claim 3, wherein the third prism and the fourth prism rotate together about the axis along the endoscope.

5. The endoscope of claim 2, wherein the first prism and the second prism comprise different refractive indices than the third prism and the fourth prism.

6. The endoscope of claim 2, wherein the first and second prisms rotate in an opposite direction than the third and fourth prisms.

7. The endoscope of claim 1, wherein the endoscope is flexible.

8. The endoscope of claim 1, wherein the first prism and the second prism are joined together by cement.

9. The endoscope of claim 1, wherein the first prism and the second prism rotate together about the axis along the endoscope.

10. The endoscope of claim 1, wherein the first prism and the second prism comprise materials with different refractive indices.

11. The endoscope of claim 1, further comprising a gear unit to rotate the first prism and second prisms.

12. A method for illuminating a visual field in an adjustable viewing direction of an endoscope, the method comprising the steps of:
   providing an illuminating light;
   providing a light splitting device positioned on the proximal end of the endoscope, the light splitting device having a first prism and second prism rotating about an axis extending from a proximal end of the endoscope to the distal end of the endoscope, and the first and second prisms being rigidly connected with one another;
   using the first prism and the second prism to switch the illuminating light that has been provided into one or more lightwave conductors associated with a first selected viewing angle;
   transmitting the illuminating light through the one or more selected lightwave conductors to one or more associated light outlet devices on the distal end of the endoscope; and
   focusing the illuminating light into the one or more light outlet devices associated with the first selected viewing angle.

13. The method of claim 12, further comprising the steps of:
   selecting a second viewing angle of the endoscope; and
   using the first and second prisms to switch the illuminating light into one or more lightwave conductors associated with the second selected viewing angle.

14. An endoscope with adjustable viewing angle, the endoscope comprising:
   a shaft having a distal end, a proximal end and an axis extending from the proximal end to the distal end;
   a light source;
   a first light outlet device on the distal end of the shaft positioned to direct illuminating light at a first angle and a second light outlet device on the distal end of the shaft positioned to direct illuminating light at a second angle;
   a first lightwave conductor for directing light to the first light outlet device and a second lightwave conductor for directing light to the second light outlet device;
   a light splitting device positioned on the proximal end of the endoscope, the light splitting device located between the light source and the first and second lightwave conductors, the light splitting device having a first prism next to the light source and a second prism between the first prism and the light wave conductors, the first and second prisms rotating about the axis extending from the proximal end to the distal end for selectively focusing the light source into the first and the second lightwave conductors;
   wherein the first and second prisms are rigidly connected with one another.

15. The endoscope of claim 14, further comprising a light inlet lens between the light source and the first prisms, the light inlet lens directing light waves from the light source to be essentially parallel with the axis prior to entering the first prism.

16. The endoscope of claim 15, further comprising a light outlet lens located between the second prism and the lightwave conductors.

17. The endoscope of claim 14, further comprising:
   a third prism and a fourth prism located between the second prism and the lightwave conductors, the third and fourth prisms rotating about the axis for selectively directing the light source into the first and second lightwave conductors in combination with the first and second prisms.

18. The endoscope of claim 17, wherein the third prism and fourth prism are rigidly connected with one another.

19. The endoscope of claim 17, further comprising:
   a light inlet lens between the light source and the first and second prisms, the light inlet lens directing light waves from the light source to be essentially parallel with the axis prior to entering the first prism.

20. The endoscope of claim 19, further comprising a light outlet lens located between the third and fourth prisms and the lightwave conductors.

21. The endoscope of claim 20, wherein the third prism and fourth prism are rigidly connected with one another.

22. The endoscope of claim 14, wherein the shaft is flexible.

* * * * *